United States Patent
Hsu et al.

(10) Patent No.: US 10,258,721 B2
(45) Date of Patent: Apr. 16, 2019

(54) PRESSURE CONTROLLER FOR PHLEGM SUCKING DEVICE

(71) Applicant: Lily Medical Corporation, Miaoli County (TW)

(72) Inventors: Tang-Lung Hsu, Miaoli County (TW); Yung-Hung Chih, Miaoli County (TW); Chih-Jung Chen, Miaoli County (TW)

(73) Assignee: Lily Medical Corporation, Miaoli County (TW)

( * ) Notice: Subject to any disclaimer, the term of this patent is extended or adjusted under 35 U.S.C. 154(b) by 0 days.

(21) Appl. No.: 15/782,942

(22) Filed: Oct. 13, 2017

(65) Prior Publication Data

US 2018/0104389 A1 Apr. 19, 2018

(30) Foreign Application Priority Data

Oct. 13, 2016 (TW) .............................. 105133043 A

(51) Int. Cl.
*A61M 1/00* (2006.01)
*F01L 3/10* (2006.01)

(52) U.S. Cl.
CPC ............. *A61M 1/0035* (2014.02); *F01L 3/10* (2013.01); *A61M 2202/04* (2013.01); *A61M 2205/3337* (2013.01)

(58) Field of Classification Search
CPC ........ A61M 1/0035; A61M 2205/3337; A61M 2202/04; A61M 1/0039; A61M 1/0041; A61M 1/0043; F01L 3/10

(Continued)

(56) References Cited

U.S. PATENT DOCUMENTS 4,316,600 A * 2/1982 Parise ...................... F16K 1/34
251/333
5,447,257 A * 9/1995 Dark ...................... B65D 83/48
251/320

(Continued)

FOREIGN PATENT DOCUMENTS

CN 204655652 U 9/2015
DE 202006018973 U1 5/2007

(Continued)

OTHER PUBLICATIONS

Office action of counterpart application by German Patent and Trademark Office dated May 23, 2018.

(Continued)

*Primary Examiner* — John Bastianelli

(57) ABSTRACT

A pressure controller for a phlegm sucking device includes a seat body, a press element and a control valve. The seat body has a containing space, a gas inlet tube and a gas outlet tube interconnected with each other. The control valve is disposed in the containing space. An upper end and a bottom end of the control valve abut the press element and an upper portion and a bottom of the seat body respectively for blocking or allowing communication between the gas inlet tube and the gas outlet tube. The control valve includes a plastic restoring element. When the plastic restoring element is deformed to have a decreased height, the plastic restoring element allows the control valve to move and provide a resilience. The control valve blocks the communication between the gas inlet tube and the gas outlet tube when the plastic restoring element is not deformed.

18 Claims, 6 Drawing Sheets

(58) Field of Classification Search
USPC ....... 251/320–323, 337; 128/207.16, 207.14; 604/119
See application file for complete search history.

(56) References Cited

U.S. PATENT DOCUMENTS

| | | | | |
|---|---|---|---|---|
| 5,755,696 | A * | 5/1998 | Caizza | A61M 25/0612 604/164.11 |
| 6,283,440 | B1 * | 9/2001 | Evans | F15C 5/00 251/11 |
| 6,681,462 | B1 * | 1/2004 | Frank | F16F 1/028 29/25.35 |
| 7,077,176 | B2 * | 7/2006 | Py | A61J 1/18 251/149.1 |
| 7,316,383 | B2 * | 1/2008 | Kegel | F02M 47/027 251/129.06 |
| 7,775,206 | B2 * | 8/2010 | Anderson | A61M 16/0463 128/200.26 |
| 7,913,974 | B2 * | 3/2011 | Smith, III | E21B 33/038 251/149.6 |
| 2004/0021123 | A1 * | 2/2004 | Howell | F16F 1/027 251/337 |
| 2004/0182393 | A1 * | 9/2004 | MacMillan | A61M 1/0043 128/205.19 |
| 2005/0263546 | A1 * | 12/2005 | Labinski | B67D 3/044 222/478 |
| 2008/0163938 | A1 * | 7/2008 | Komara | A01G 25/02 137/511 |
| 2009/0005746 | A1 * | 1/2009 | Nielsen | A61M 1/0031 604/315 |
| 2010/0274199 | A1 * | 10/2010 | Weston | A61M 5/326 604/198 |
| 2011/0233439 | A1 | 9/2011 | Lee | |
| 2011/0309279 | A1 * | 12/2011 | Richards | B67D 7/0294 251/149.7 |
| 2013/0296816 | A1 * | 11/2013 | Greener | A61M 1/0031 604/320 |
| 2015/0102245 | A1 * | 4/2015 | Chen | A61M 39/10 251/149 |

FOREIGN PATENT DOCUMENTS

| | | |
|---|---|---|
| JP | H08071462 A | 3/1996 |
| JP | 2012233517 A | 11/2012 |
| TW | M477890 U | 5/2014 |
| TW | M480392 U | 6/2014 |

OTHER PUBLICATIONS

Office action of counterpart application by Japan IP Office dated Sep. 25, 2018.

* cited by examiner

PRESSURE CONTROLLER FOR PHLEGM SUCKING DEVICE

This application claims the benefit of Taiwan application Serial No. 105133043, filed Oct. 13, 2016, the subject matter of which is incorporated herein by reference.

BACKGROUND OF THE INVENTION

Field of the Invention

The invention relates in general to a pressure controller for a phlegm sucking device, and more particularly to a pressure controller for a phlegm sucking device whose structural material has stable properties.

Description of the Related Art

To suck the phlegm from a patient, normally a phlegm sucking tube is inserted into the patient's respiratory tract, and a negative pressure is generated by a pressure generator and used as a power source for the phlegm sucking tube. A pressure controller is disposed between the pressure generator and the phlegm sucking tube for blocking or allowing the communication between the phlegm sucking tube and the pressure generator. Normally, the pressure controller for a phlegm sucking device uses a metal spring as a restoring element which allows the user to control the ON/OFF state of gas vacuuming. Since the metal material may easily react with the gas and/or the liquid, the gas and/or the liquid passing through the metal material, the gas and/or the liquid may react with the elements of the device, make the elements become deteriorated (for example, get rusty or corroded), affect the lifespan of the device or increase the user's chance of infection. Besides, the metal material may interfere with adjacent electronic devices and affect the operation. Moreover, the control valve between the metal spring restoring element and the pressure controller is a separation element, and requires a complex assembly operation.

SUMMARY OF THE INVENTION

The present invention is directed to a pressure controller for a phlegm sucking device capable of resolving the problems encountered in the prior art.

According to one embodiment of the present invention, a pressure controller for a phlegm sucking device is provided, including a seat body, a press element and a control valve. The seat body has a containing space, a gas inlet tube and a gas outlet tube interconnected with each other. The control valve is disposed in the containing space of the seat body. An upper end and a bottom end of the control valve abut the press element and an upper portion and a bottom of the seat body respectively for blocking or allowing communication between the gas inlet tube and the gas outlet tube. The control valve comprises a plastic restoring element, a valve bolt and a valve stem. When the plastic restoring element is deformed due to being pressed to have a decreased height, the plastic restoring element allows the control valve to move with the decreased height and provide a resilience for recovery. The valve bolt is interposed between the gas inlet tube and the gas outlet tube. The valve stem is disposed above the plastic restoring element. The valve stem is plugged in the valve bolt and extended beyond the containing space of the seat body and abuts the press element. When the plastic restoring element is not deformed, the valve bolt encloses at least one of a junction between the gas inlet tube and the containing space, a junction between the gas outlet tube and the containing space, and a sidewall of the containing space to block the communication between the gas inlet tube and the gas outlet tube. When the press element is pressed, the valve stem is moved with the pressed press element so as to deform the plastic restoring element, and the valve bolt shifts correspondingly to make the gas inlet tube communicate with the gas outlet tube without generating a deformation to the valve bolt.

According to one embodiment of the present invention, a pressure controller for a phlegm sucking device is provided, including a seat body, a press element and a control valve. The seat body has an inner-wall defining a containing space, a gas inlet tube and a gas outlet tube interconnected with each other. The control valve is disposed in the containing space of the seat body. An upper end and a bottom end of the control valve abut the press element and an upper portion and a bottom of the seat body respectively. The control valve comprises a restoring element and a cone shape portion. The restoring element is deformed due to pressing the press element to have a decreased height. The restoring element allows the control valve to move with the decreased height and provide a resilience for recovery. The cone shape portion is over the restoring element, and having a radial size decreasing gradually along a direction away from the restoring element, and is for blocking or allowing communication between the gas inlet tube and the gas outlet tube. The inner-wall of the seat body has a cone shape matching the cone shape portion of the control valve. When the restoring element is not deformed, the control valve blocks the communication between the gas inlet tube and the gas outlet tube. When the restoring element is deformed, the control valve shifts correspondingly to make the gas inlet tube communicate with the gas outlet tube.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
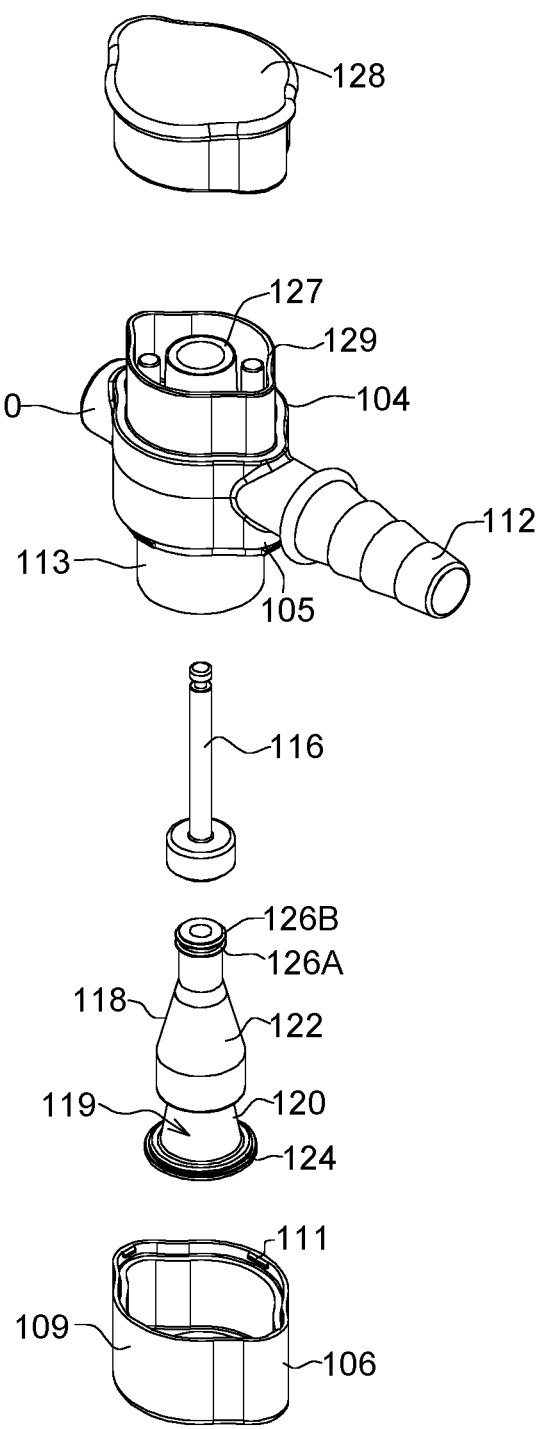
FIG. 1 is an explosion diagram of a pressure controller for a phlegm sucking device according to an embodiment.
Figure 2:
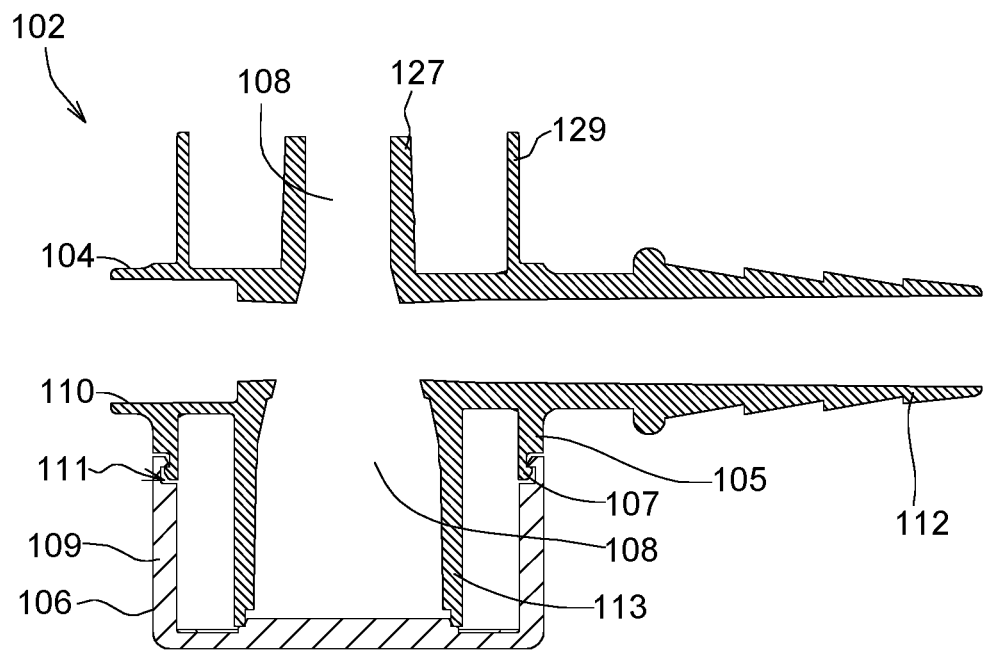
FIG. 2 is a cross-sectional view of a seat body according to an embodiment.

Refer to FIG. 1 and FIG. 2. The seat body 102 of the pressure controller for a phlegm sucking device includes a cylinder portion 104 and a base 106. The cylinder portion 104 has a containing space 108, a gas inlet tube 110 and a gas outlet tube 112, interconnected with each other. The bottom of the lower outer-wall 105 of the cylinder portion 104 (FIG. 2) has a hook 107 engaged with the indent 111 of the seat wall 109 of the base 106, such that the cylinder portion 104 and the base 106 are jointed together.

Figure 3:
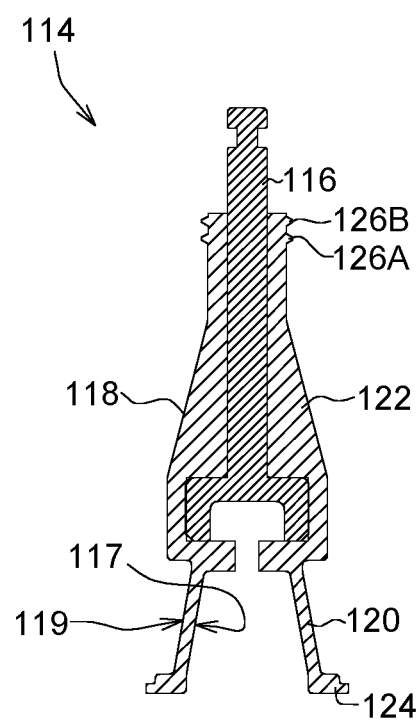
FIG. 3 is a cross-sectional view of a control valve according to an embodiment.

Refer to FIG. 1 and FIG. 3. The control valve 114 of the pressure controller for a phlegm sucking device includes a valve stem 116 and a valve body 118. The valve body 118 includes a restoring element 120, and a valve bolt 122 and a seal element 124. The valve bolt 122 and the seal element 124 are respectively connected to opposing sides of the restoring element 120. The seal element 124 is laterally extended from the bottom of the restoring element 120 and surrounds the peripheral edge of the restoring element 120. The outer surface of the upper portion of the valve bolt 122 has an annular flange 126A and an annular flange 126B separated by an interval. The valve stem 116 can be plugged on the valve bolt 122 and protruded from the valve bolt 122.

In the present embodiment, the restoring element 120 has a hollow cone shape wide at the bottom and narrow at the top, and has an even inner surface 117 and an even outer surface 119.

In an embodiment, the valve body 118 is integrally formed in one piece by way of injection. In other words, the restoring element 120, the valve bolt 122, the seal element 124 and the annular flanges 126A and 126B are formed of the same material and constitute one single piece. Thus, the manufacturing method of the valve body 118 is simple and quick and the manufacturing cost is lowered. In this way, total number of elements of the pressure controller for a phlegm sucking device (in an embodiment as indicated in FIG. 1, the pressure controller for a phlegm sucking device is formed of 5 elements, including the press element 128, the cylinder portion 104, the valve stem 116, the valve body 118 and the base 106, but the present disclosure is not limited thereto) can be reduced, the assembly is convenient and the manufacturing cost is lowered.

For example, the valve body 118 can be formed of a non-metal plastic, such as a plastic having low reactivity with the gas, such that the problems of gas pollution or deterioration of the valve body 118 arising from the reaction can be avoided, the gas-vacuuming system can be stabilized and the lifespan of the product can be prolonged. The plastic may include an non-conductive material having a stable property, for example, comprising a silicon, a thermosetting rubber, or other types of rubbers, such as a thermoplastic elastomer (TPE), such as a thermoplastic rubber (TPR), or a thermoplastic polyurethane (TPU), a thermoplastic polyolefin (TPO), a thermoplastic vulcanizate (TPV), etc.

Figure 4:
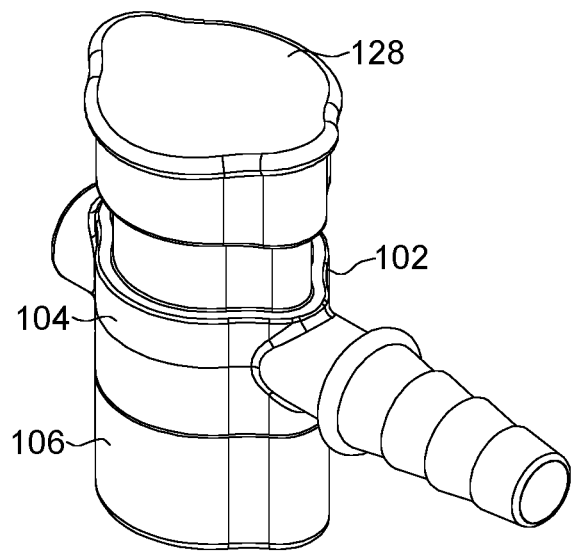
FIG. 4 is an external view of a pressure controller for a phlegm sucking device not being pressed according to an embodiment.
Figure 5:
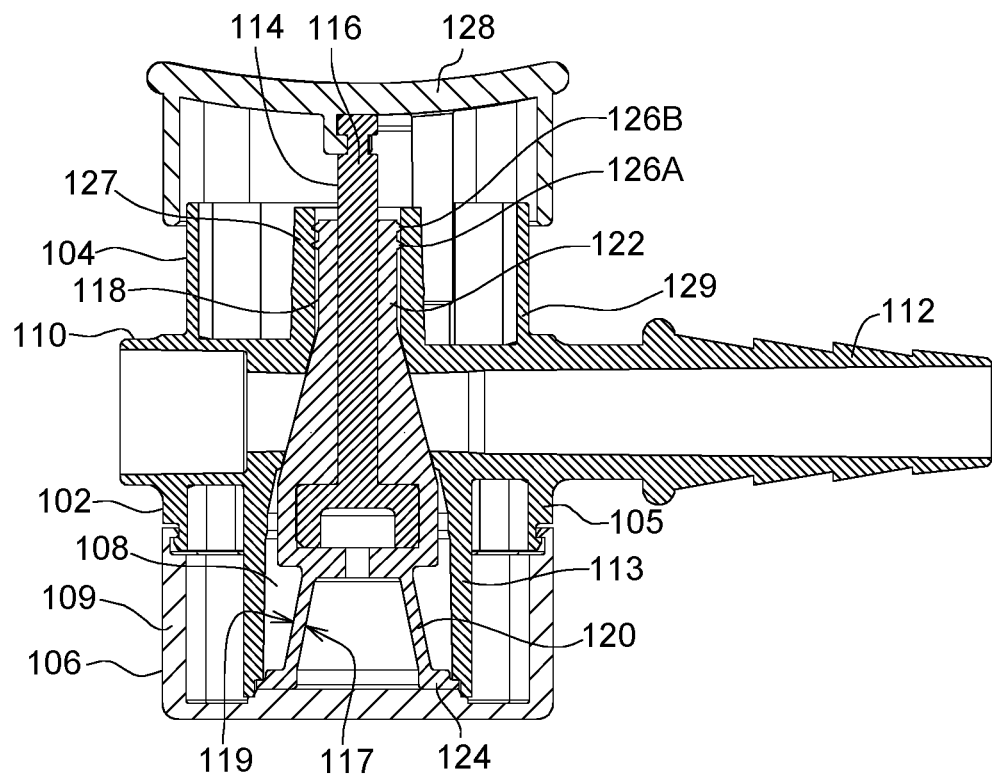
FIG. 5 is a cross-sectional view of a pressure controller for a phlegm sucking device not being pressed according to an embodiment.

Refer to FIG. 4 and FIG. 5. The control valve 114 is disposed in the containing space 108 of the seat body 102, wherein the valve stem 116 is extended beyond the containing space 108 and protruded from the upper inner-wall 127 and the upper outer-wall 129 of the seat body 102. The valve stem 116 and the seal element 124 disposed at the upper end and the bottom end of the control valve 114 respectively abut the press element 128 and the inner surface of the base 106 of the seat body 102. The seal element 124 is interposed between the inner surface of the lower inner-wall 113 of the cylinder portion 104 and the inner surface of the bottom of the base 106 to seal the cylinder portion 104 and the base 106. When the press element 128 is not pressed by the user, the valve bolt 122 of the control valve 114 encloses at least one of the junction between the gas inlet tube 110 and the containing space 108, the junction between the gas outlet tube 112 and the containing space 108, and the sidewall of the containing space 108 (or define the inner sidewall of the cylinder portion 104 of the containing space 108) to block the communication between the gas inlet tube 110 and the gas outlet tube 112, such that the gas cannot flow between the gas inlet tube 110 and the gas outlet tube 112, and gas-vacuuming is suspended. The annular flanges 126A and 126B separated by an interval are disposed on an outer surface of the valve bolt 122 above the gas inlet tube 110 and the gas outlet tube 112. The annular flanges 126A and 126B contact the inner surface of the upper inner-wall 127 of the cylinder portion 104 to enhance the air-tight effect of the cylinder portion 104 during the movement of the valve body 118.

Figure 6:
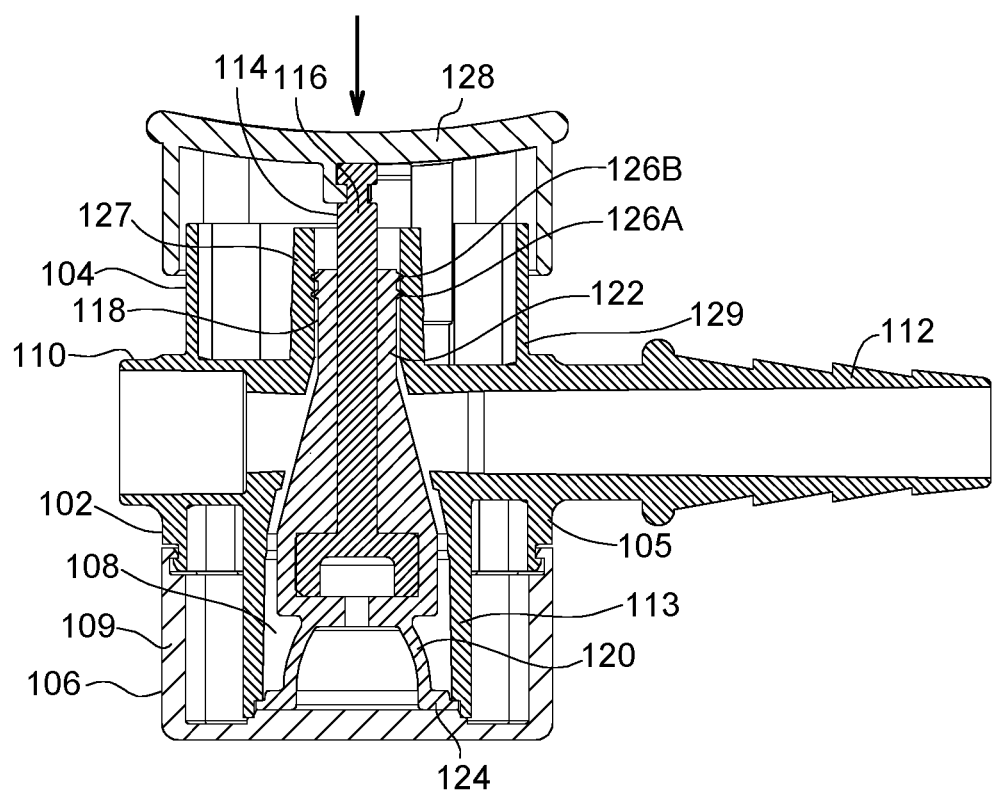
FIG. 6 is a cross-sectional view of a pressure controller for a phlegm sucking device being pressed according to an embodiment.

Refer to FIG. 6. When the press element 128 is pressed by the user, the restoring element 120 disposed in the containing space 108 under the gas inlet tube 110 and the gas outlet tube 112 is deformed to have a decreased height, and allows the control valve 114 to move downward with the decreased height. After the control valve 114 moves downwards, the valve bolt 122 will not enclose any of the junction between the gas inlet tube 110 and the containing space 108, the junction between the gas outlet tube 112 and the containing space 108, and the sidewall of the containing space 108, such that the gas inlet tube 110 and the gas outlet tube 112 are interconnected, the gas can flow between the gas inlet tube 110 and the gas outlet tube 112 and be vacuumed. Meanwhile, the upper part of the valve bolt 122 on which the annular flanges 126A and 126B are disposed still contacts the upper inner-wall 127, and the seal element 124 still tightly seals the junction between the cylinder portion 104 and the base 106, such that gas can flow between the gas inlet tube 110 and the gas outlet tube 112 and will not leak off the pressure controller for a phlegm sucking device.

When the user releases the press element 128, the restoring element 120 provides a resilience restoring the control valve 114 upward to the state as illustrated in FIG. 5.

In other embodiments, the control valve can be designed to have other shapes according to actual needs.

Figure 7A:
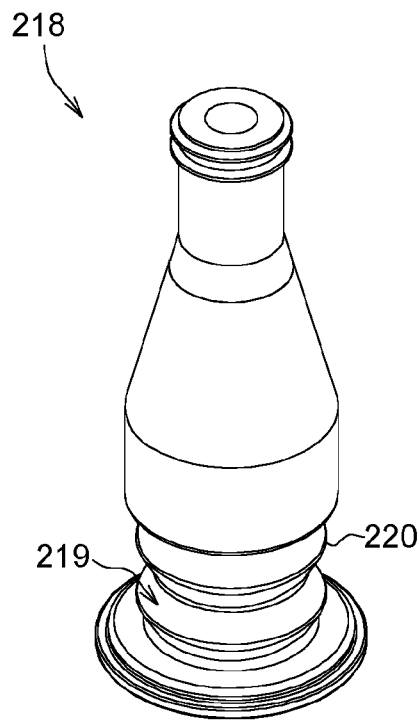
FIG. 7A is a 3D diagram of a valve body of a control valve according to an embodiment.
Figure 7B:
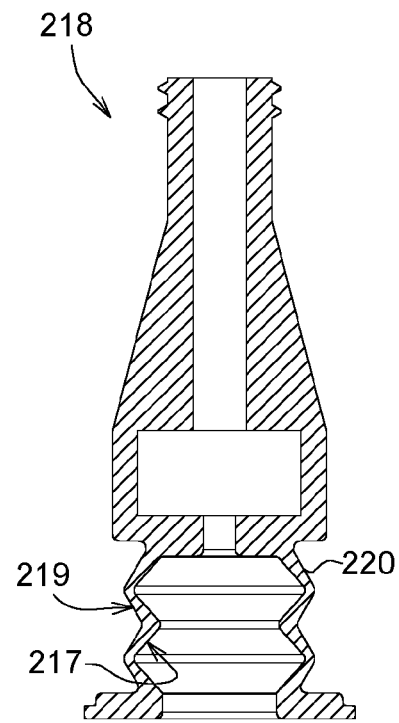
FIG. 7B is a cross-sectional view of the valve body of FIG. 7A.

FIG. 7A and FIG. 7B respectively are a 3D diagram and a cross-sectional view of a valve body 218 used in a control valve according to an embodiment. The valve body 218 of the present embodiment is different from the valve body 118 in that the restoring element 220 has a bumpy inner surface 217 and a bumpy outer surface 219, wherein the protrusion of the outer surface 219 corresponds to the indentation of the inner surface 217, and the indentation of the outer surface 219 corresponds to the protrusion of the inner surface 217.

Figure 8A:
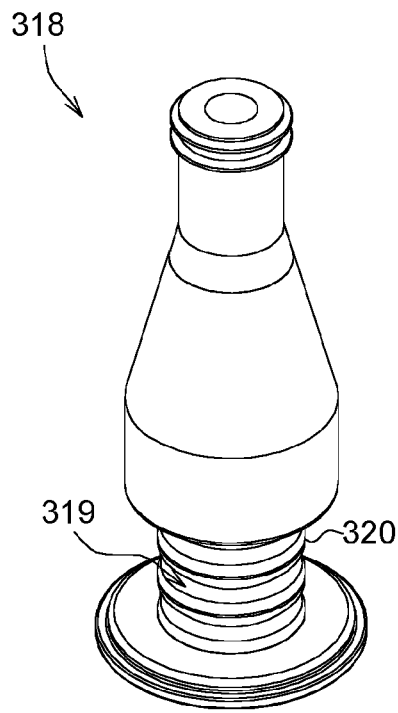
FIG. 8A is a 3D diagram of a valve body of a control valve according to an embodiment.
Figure 8B:
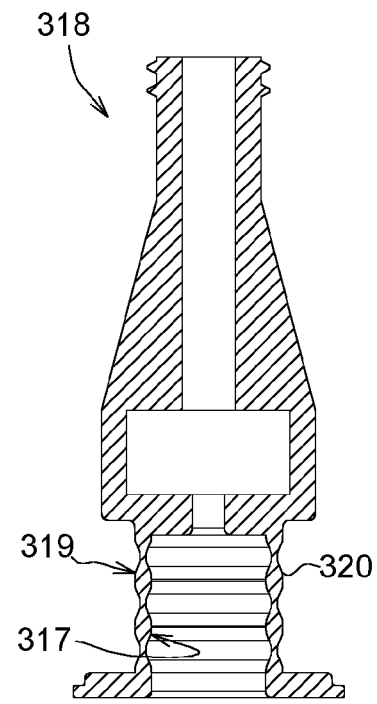
FIG. 8B is a cross-sectional view of the valve body of FIG. 8A.

FIG. 8A and FIG. 8B respectively are a 3D diagram and a cross-sectional view of a valve body 318 according to an embodiment. The valve body 318 of the present embodiment is different from the valve body 218 of FIG. 7A and FIG. 7B in that in the restoring element 320, the protrusion of the outer surface 319 9 corresponds to the protrusion of the inner surface 317, and the indentation of the outer surface 319 corresponds to the indentation of the inner surface 317.

Figure 9:
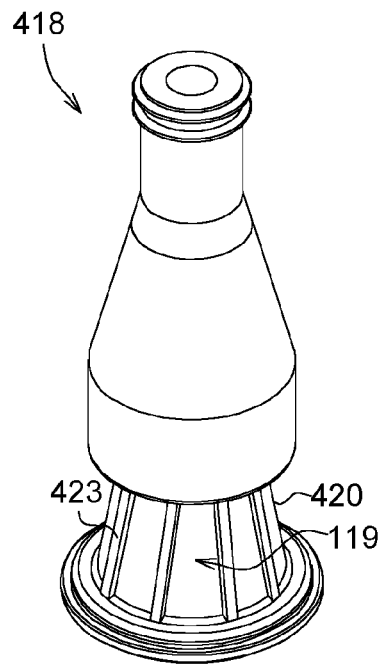
FIG. 9 is a 3D diagram of a valve body of a control valve according to an embodiment.

FIG. 9 is a 3D diagram of a valve body 418 according to an embodiment. The valve body 418 of the present embodiment is different from the valve body 118 in that the valve body 418 further includes a number of longitudinal ribs 423 protruded from the outer surface 119 and spaced at regular intervals. The ribs 423 can enhance the resilience generated when the restoring element 420 is pressed and deformed.

Figure 10:
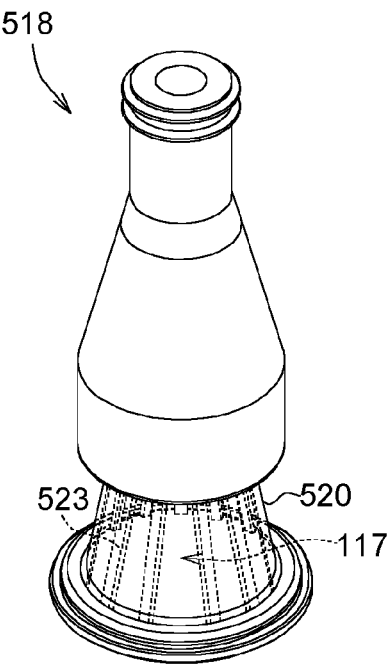
FIG. 10 is a 3D diagram of a valve body of a control valve according to an embodiment.

FIG. 10 is a 3D diagram of a valve body 518 according to an embodiment, wherein the restoring element 520 is illustrated in the manner of perspective. The valve body 518 of the present embodiment is different from the valve body 118 in that the valve body 518 further includes a number of longitudinal ribs 523 protruded from the inner surface 117 and spaced at regular intervals the. The ribs 523 can enhance the resilience generated when the restoring element 520 is pressed and deformed.

Figure 11:
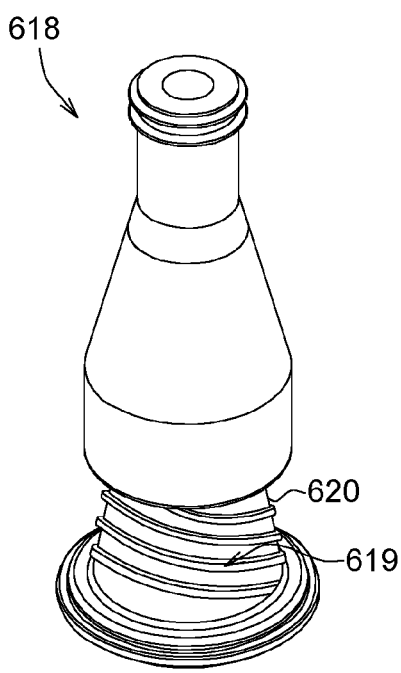
FIG. 11 is a 3D diagram of a valve body of a control valve according to an embodiment.

FIG. 11 is a 3D diagram of a valve body 618 according to an embodiment. The valve body 618 of the present embodiment is different from the valve body 118 in that the restoring element 620 has a threaded outer surface 619.

According to the embodiments disclosed above, the pressure controller for a phlegm sucking device uses a restoring element, has stable properties and long lifespan, avoids interfering with the gas or adjacent electronic devices, and therefore has high safety in terms of use. Moreover, the restoring element and other elements of the control valve can be integrally formed in one piece, such that the total number of elements of the pressure controller for a phlegm sucking device can be reduced, the manufacturing method is simple and quick and the manufacturing cost is lowered.

While the invention has been described by way of example and in terms of the preferred embodiment (s), it is to be understood that the present disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A pressure controller for a phlegm sucking device, comprising:
   a seat body having a containing space, a gas inlet tube and a gas outlet tube interconnected with each other;
   a press element; and
   a control valve disposed in the containing space of the seat body, wherein an upper end and a bottom end of the control valve abut the press element and a bottom of the seat body respectively for blocking or allowing communication between the gas inlet tube and the gas outlet tube, the control valve comprises:
   a rubber restoring element, wherein when the rubber restoring element is deformed due to being pressed to have a decreased height, the rubber restoring element allows the control valve to move with the decreased height and provide a resilience for recovery;
   a valve bolt interposed between the gas inlet tube and the gas outlet tube; and
   a valve stem disposed above the rubber restoring element, wherein the valve stem is plugged in the valve bolt and extended beyond the containing space of the seat body and abuts the press element,
   wherein when the rubber restoring element is not deformed, the valve bolt encloses at least one of a junction between the gas inlet tube and the containing space, and a junction between the gas outlet tube and the containing space to block the communication between the gas inlet tube and the gas outlet tube, and when the press element is pressed, the valve stem is moved with the pressed press element so as to deform the rubber restoring element, and the valve bolt shifts correspondingly to make the gas inlet tube communicate with the gas outlet tube without generating a deformation to the valve bolt, and all of the valve bolt on a the valve stem is integrally formed in one piece, an empty space defined within an inner surface of the rubber restoring element is isolated from an outer surface of the rubber restoring element.

2. The pressure controller for the phlegm sucking device according to claim 1, wherein the rubber restoring element is a hollow body.

3. The pressure controller for the phlegm sucking device according to claim 1, wherein the rubber restoring element has a hollow cone shape.

4. The pressure controller for the phlegm sucking device according to claim 1, wherein the rubber restoring element has a cone shape wide at the bottom and narrow at the top.

5. The pressure controller for the phlegm sucking device according to claim 1, wherein the rubber restoring element has a threaded outer surface.

6. The pressure controller for the phlegm sucking device according to claim 1, wherein the rubber restoring element has ribs spaced at regular intervals on the inner surface of the rubber restoring element.

7. The pressure controller for the phlegm sucking device according to claim 6, wherein the ribs comprise longitudinal ribs.

8. The pressure controller for the phlegm sucking device according to claim 6, wherein the ribs enhances the resilience of the rubber restoring element being pressed and deformed.

9. The pressure controller for the phlegm sucking device according to claim 1, wherein a material of the rubber restoring element comprises a thermosetting rubber, or a thermoplastic rubber.

10. The pressure controller for the phlegm sucking device according to claim 1, wherein the rubber restoring element is disposed in the containing space under the gas inlet tube and the gas outlet tube.

11. The pressure controller for the phlegm sucking device according to claim 1, wherein an outer surface of the valve bolt has at least one annular flange.

12. The pressure controller for the phlegm sucking device according to claim 11, wherein the valve bolt and the at least one annular flange are integrally formed in one piece by way of injection.

13. The pressure controller for the phlegm sucking device according to claim 1, further comprising a seal element laterally extended from the bottom of the rubber restoring element to seal a junction between the bottom of the seat body and a sidewall of the seat body.

14. The pressure controller for the phlegm sucking device according to claim 13, wherein the seal element surrounds a peripheral edge of the rubber restoring element.

15. The pressure controller for the phlegm sucking device according to claim 14, wherein the rubber restoring element, the valve bolt and the seal element are integrally formed in one piece.

16. The pressure controller for the phlegm sucking device according to claim 1, wherein the rubber restoring element and the valve bolt are integrally formed in one piece.

17. The pressure controller for the phlegm sucking device according to claim 1, wherein the rubber restoring element has an outer surface, the outer surface is an even outer surface or a bumpy outer surface, and the inner surface of the rubber restoring element is an even inner surface or a bumpy inner surface.

18. The pressure controller for the phlegm sucking device according to claim 9, wherein the material of the rubber restoring element comprises the thermoplastic rubber comprising a thermoplastic polyurethane, a thermoplastic polyolefin, or a thermoplastic vulcanizate.

\* \* \* \* \*